US008100576B2

(12) United States Patent
Cartagena et al.

(10) Patent No.: US 8,100,576 B2
(45) Date of Patent: Jan. 24, 2012

(54) METHOD AND APPARATUS FOR PREPARATION OF GRANULATED MATERIAL

(76) Inventors: Gustavo Cartagena, Santiago (CL); Victor Cordova, Santiago (CL)

( * ) Notice: Subject to any disclaimer, the term of this patent is extended or adjusted under 35 U.S.C. 154(b) by 910 days.

(21) Appl. No.: 12/119,761

(22) Filed: May 13, 2008

(65) Prior Publication Data

US 2008/0298166 A1     Dec. 4, 2008

(30) Foreign Application Priority Data

May 28, 2007   (CL) .................................. 1519-2007

(51) Int. Cl.
*B01F 11/00* (2006.01)
*B01F 15/02* (2006.01)

(52) U.S. Cl. .................. 366/140; 366/153.2; 366/153.3; 366/184

(58) Field of Classification Search .................. 366/140, 366/150.1, 153.2, 153.3, 184
See application file for complete search history.

(56) References Cited

U.S. PATENT DOCUMENTS

| | | | | |
|---|---|---|---|---|
| 692,774 A | * | 2/1902 | Appleby | 366/133 |
| 742,385 A | * | 10/1903 | Blaisdell | 366/169.1 |
| 979,685 A | * | 12/1910 | Mumford | 209/323 |
| 1,011,380 A | * | 12/1911 | Sidwell | 34/172 |
| 3,166,300 A | * | 1/1965 | Richter | 366/153.2 |
| 4,715,722 A | * | 12/1987 | Hergeth et al. | 366/132 |
| 4,744,459 A | | 5/1988 | Ryan | |
| 4,966,463 A | * | 10/1990 | Hihara et al. | 366/3 |
| 6,123,447 A | * | 9/2000 | Schelhorn | 366/153.2 |
| 2007/0138407 A1 | | 6/2007 | Mcinnes et al. | |
| 2008/0298166 A1 | * | 12/2008 | Cartagena et al. | 366/140 |

FOREIGN PATENT DOCUMENTS

| | | |
|---|---|---|
| AU | 2004308157 A1 | 7/2005 |
| CL | 2687-2004 | 10/2004 |
| GB | 946573 | 1/1964 |
| WO | 2005062702 A2 | 7/2005 |

* cited by examiner

*Primary Examiner* — Tony G Soohoo
(74) *Attorney, Agent, or Firm* — McGarry Bair PC

(57) ABSTRACT

An apparatus for preparing samples of granulated material comprises an upper vessel having a floor including a plurality of planks, slots between each plank, and an open ceiling to allow passing of homogenized material, a lower vessel under the upper vessel and having a plurality of division plates that fit in the slots and form a plurality of compartments which hold samples, a feeder which oscillates over the upper surface of the upper vessel to render a homogenised and representative sample. The method comprises positioning the lower vessel under the upper vessel, feeding material to be sampled through the feeder by an oscillating movement, raising the lower vessel such that the division plates partition the heap of material to form a plurality of samples, removing planks from the upper vessel, thus forcing the plurality of samples to fall toward the compartments, and separating both the vessels to remove the samples.

6 Claims, 6 Drawing Sheets

METHOD AND APPARATUS FOR PREPARATION OF GRANULATED MATERIAL

CROSS-REFERENCE TO RELATED APPLICATION

This application claims the benefit of Chilean Application No. 1519-2007 filed May 28, 2007 and incorporated by reference in its entirety.

FIELD OF THE INVENTION

The present disclosure relates to a method and apparatus for automatic preparation of samples.

BACKGROUND OF THE DISCLOSURE

The industry in general, and in particular the mining industry, requires knowing the composition of material processed. Knowing the composition, forces the collection of samples that are submitted to laboratories for analysis purposes. Currently there are a several methods for sample collection which are highly disseminated. These methods are the outcome from research and investigation works conducted by Professors Francis Pitard and Pierre Guy. Current sampling methods consist of taking part of the material under study as to determine the content of elements relevant to the economic processing of the material. This part which is extracted from the material is referred to as sample and its validity as to represent all the material depends on size and physical process conducted to obtain it. The sample collection process implies the possibility that relevant components of the material, present in the sample, have values that fall within a high range, thus do not represent the actual content of components in the total amount of the material. Such variability is rather convenient from the perspective of processes to be applied to the material.

Patent application CL 2687-2004 (McInnis et al.) dated Oct. 20, 2004, discloses a stock apparatus for samples of fluent solid material which includes a body which has in its upper part a delivery opening under which a deflector deviates the sample towards a canister, wherein said canister has its own means to be moved over a collection means, wherein the means have a tube which discharges the stock. The body holds in its upper part an opening which expels waste in the lower end of said body, waste which was not collected as sample by the canister. The invention disclosed in the document herein allows having a mechanism to ensure the collection of a random sample representing material captured through the upper opening of the body.

U.S. Pat. No. 4,744,459 (Ryan) dated May 17, 1988 discloses a method and apparatus to shape heaps of samples of material accumulated, from a flowing solid material. The apparatus comprises a large structure which holds within a moving conveyor system which enables the creation of solid material heaps. Flowing solid material is carried from two halves arranged on opposite sides of a vertical symmetry plane along the length of the apparatus. Such material is built up by conveying a portion of material fed through a long transporting system arranged and running within the apparatus. There are discharge ducts to dump the material on two cross-conveyor systems. The discharging ends of the conveyors move closer or further from the plane of symmetry thus forming long heaps, first on the floor thus covering both sides of the plane of symmetry with fluid material layers formed by the heaps. The position of cross-conveyors is changed upon completion of each front movement and each round movement as to make different layers on the heaps.

Patent GB 946573 (Bolidens Gruv AB) dated Jan. 15, 1964 discloses an apparatus for sampling of a current of particles in free fall and which pass through a box holding a funnel wherein the sample falls and is dragged toward the funnel by a mechanically acted arm. The funnel connects a tube which conveys the sample towards the lower part of the box wherein a base comprising two compartments in one of the sides therein, and the base moves in oscillation forcing the sample to fall in the compartments, thus forming a heap between both compartments.

There are numerous apparatus in the previous art which allow to collect representative samples, but in general such apparatus are very complex and with high cost. These apparatus do not allow obtaining a plurality of representative samples which are useful for both analytical and storing purposes of core samples.

SUMMARY

The present invention is related to a method and apparatus to obtain a plurality of samples at low cost, thus rendering the possibility of using such samples for both analysis and storage of core samples.

The apparatus comprises two vessels and one feeding mechanism wherein the vessel receives and makes the material homogeneous, wherein said lower vessel holds a plurality of plates which subdivides therein in compartments where homogenous material is received from the upper vessel. The apparatus of the present invention is primarily applied to the mining industry where it is necessary to know the composition of materials processed The automatic sampler is based on the mechanism of homogenization heap building using the Chevron method. The homogenization heap building referred as Chevron consists of laying the material to be render homogeneous over a surface area through a feeding system which is moving from one end to the other end of the heap by covering a circuit along the main axis of the heap. Thus, several layers of material are built with each pass. The material placed is extracted from heaps which are cut following a specific cross-section width with respect to the main axis. Each slice produced has the particularity that is homogeneous in terms of fractions of elements which form the material. Based on the mechanism of construction and material extraction from the heap, an apparatus has been conceived as to obtain the samples. The apparatus consists of a material dispenser or feeder and two vessels. The vessels have length l, height h, and width s and are arranged one above the other. The vessel located in the upper part plays the role of forming and containing the heap of material to be sampled while the vessel located in the lower part of the assembly receives the material in compartments which simulate the slices to extract; the feeder shapes the heap in the upper vessel. The material placed within each compartment of the lower vessel becomes a sample which represents the total amount of the material which has been already homogenized. The invention facilitates sampling material fed by conveyor belts, blast holes, drillings or feeders to large processes of mining of material.

BRIEF DESCRIPTION OF THE DRAWINGS

The drawings, which are included as to provide greater understanding of the invention, are herein incorporated and are integral part of the description and illustrate one embodiment of the invention, and along with the description, facilitate the explanation of the principles of the invention.

DESCRIPTION OF THE INVENTION

Figure 1:
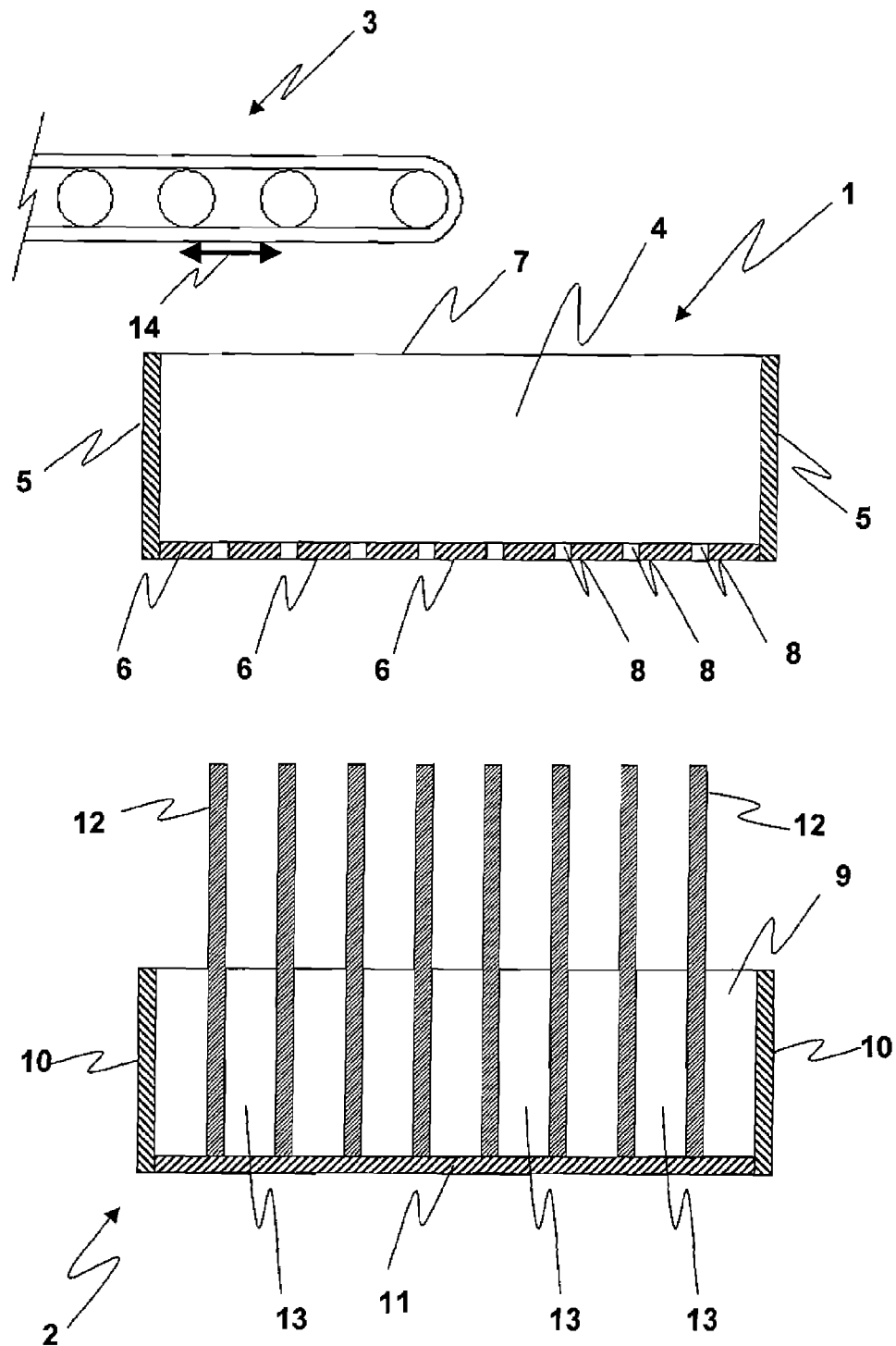
FIG. 1 shows an expanded, schematic view of upper vessel, the lower vessel, and the division plates therein and the conveyor for material.

The present invention relates to a method and apparatus to prepare samples of granulated material, which is based on the mechanism of construction of heaps of homogenization by using the method of Chevron. The apparatus consists of a material feeder and two vessels with length "l", height "h", and width "s", arranged one above the other. The upper vessel has the purpose of forming the heap by using the feeder and the lower vessel, and comprises plates therein which make compartments and which, when moved in an upward direction makes the material present in the upper vessel to be separated within the compartments and which can then be received by the lower vessel, thus becoming a sample from the material filling each compartment. As the material existing in the upper vessel is homogeneous, then portions from each compartment in the lower vessel are also homogeneous, thus forming samples with appropriate size and reliable to be analysed as the process of homogenization has removed variability. Homogenization of material present in the upper vessel depends on the length of the vessel, the rate of the feeder, and on the feeding rate of the material. By using a mathematical model in the computer the process of filling-up of the heap is simulated in order to determine the length of the heap, filling rate of the feeder, and the feeding rate, factors that ensure a good homogenization and thus making the material present in any given compartment to be a representative sample.

Based on the illustrations presented by the Figures, the apparatus for sample preparation comprises two vessels 1, 2, and a feeder 3. The upper vessel 1 receives and homogenizes the material 15. The lower vessel 2 consists of two plates 12 which subdivide the lower vessel therein in compartments 13 where homogenized material is fed from the upper vessel 1. The feeder 3 distributes the material in the upper vessel by performing an oscillating movement 14 along the length of the upper vessel, wherein the movement of the feeder is a repetitive movement coming and going along the length of the upper vessel 1. The material received at any given compartment 13 of the lower vessel 1 forms a representative sample of the total wherein each sample which is required to be remove for analytical purposes or storage is removed by gates located at the base of each compartment.

FIG. 1 illustrates the three members which comprise the apparatus for preparing samples of granulated material of the present invention. The upper vessel 1 consists of major walls 4 and minor walls, wherein the floor consists of a plurality of planks 6 which have a slot 8 between each of the planks. The ceiling of the upper vessel 7 is open as to allow passing of the sample which is then homogenized within the upper vessel 1.

Under and below the upper vessel 1 the lower vessel 2 is arranged and consists of major walls 9 and minor walls 10, and a floor 11. Inside the lower vessel 2 there is an arrangement of separation plates 12 which present a greater height than both the major walls 9 and the minor walls 10 as to be projected over the upper portion of the lower vessel 2 and fit into the slots 8. The plurality of division plates 12 forms within the lower vessel 2 a plurality of compartments 13 that will hold the plurality of samples.

The material 15 is fed by the feeder 3 which has an oscillating movement 14 over the upper surface of the upper vessel 1 and which movement and speed had been previously computed as to ensure rendering of a homogenized and representative sample 15 as per the method of Chevron.

Figure 2:
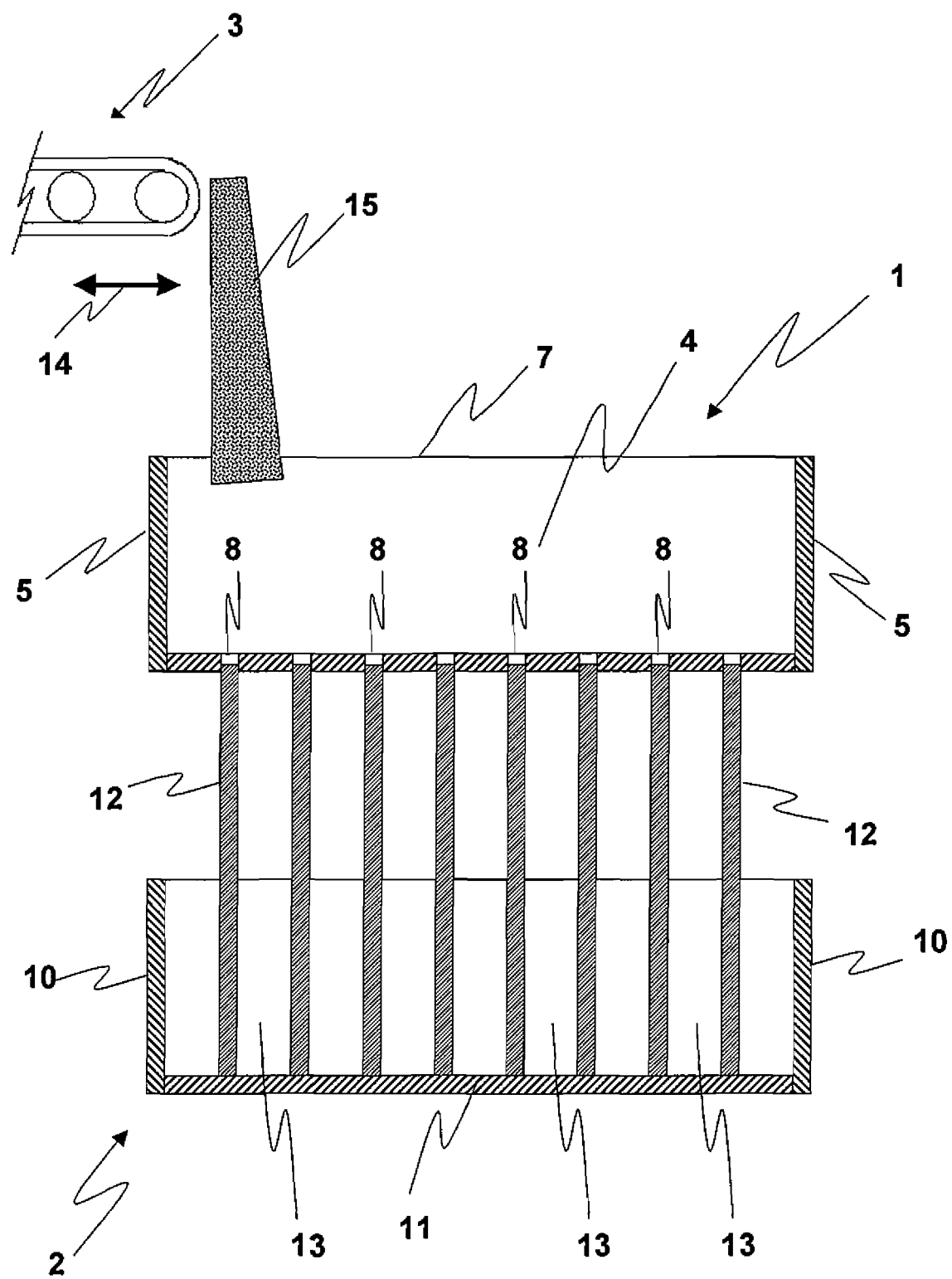
FIG. 2 shows a schematic view of the lower vessel with the plates therein inserted in the floor of the upper vessel and the conveyor for the material arranged on and above the first end of the upper vessel pouring the material.
Figure 3:
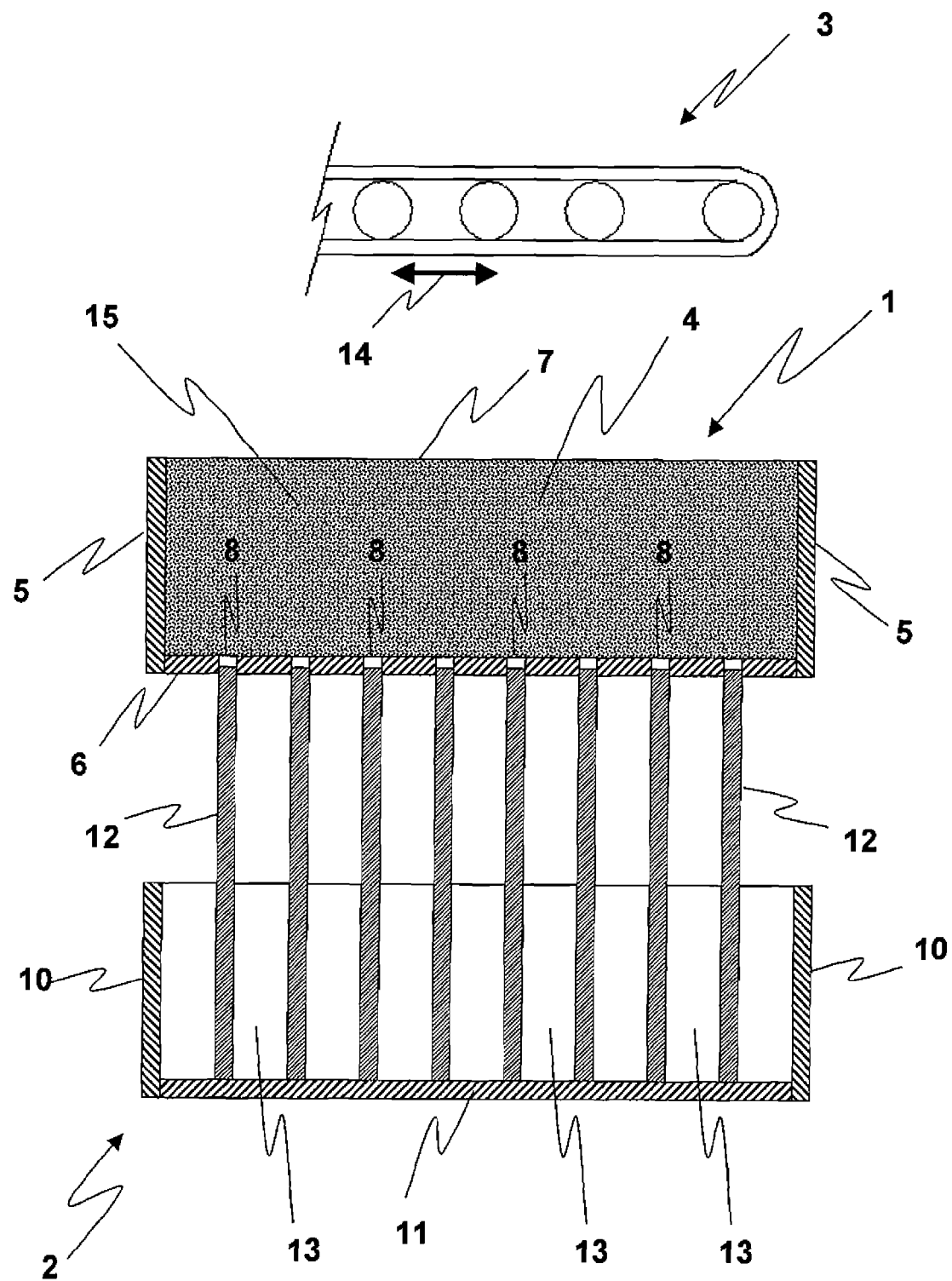
FIG. 3 illustrates a schematic view of the upper vessel, inserted in the lower vessel and the division plates therein, as well as the conveyor for the material arranged on and over the second end of the upper vessel pouring material to show the filling effect with produced by the oscillating movement of the conveyor.
Figure 4:
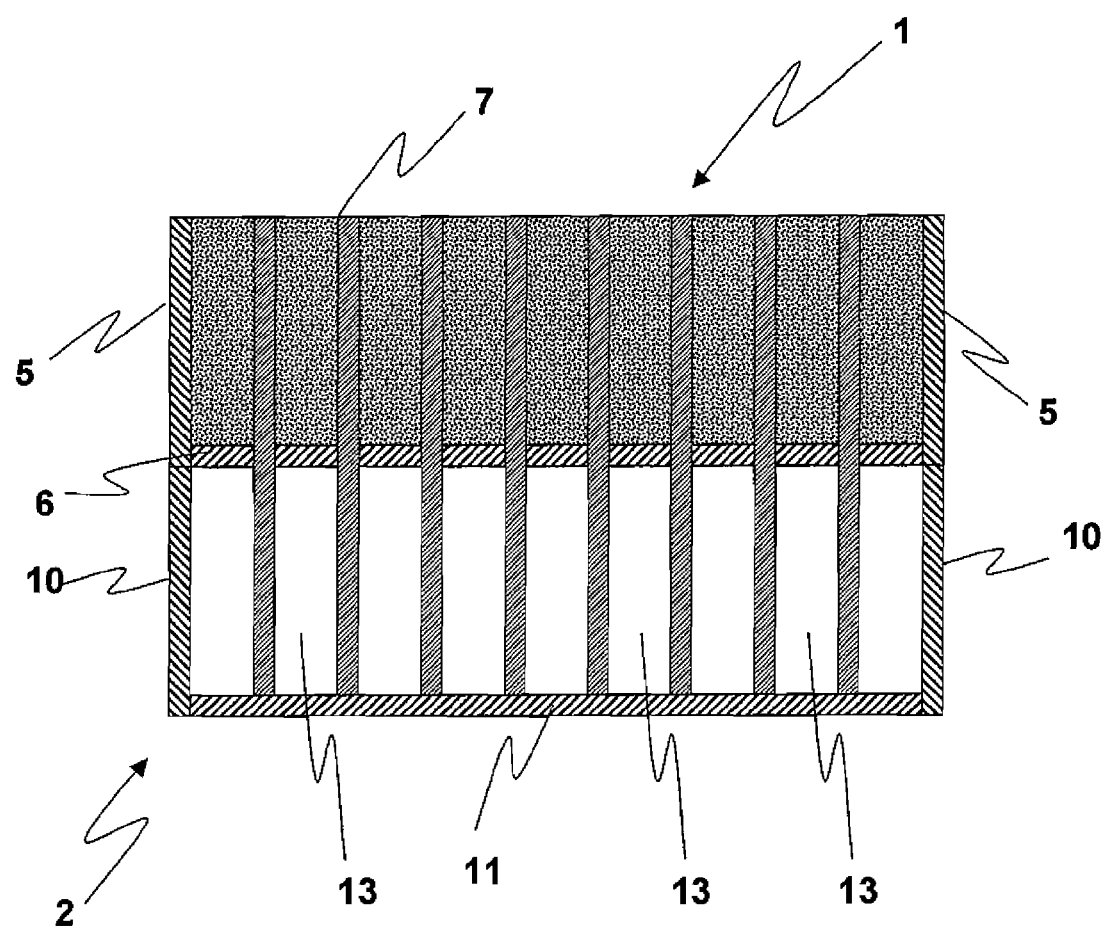
FIG. 4 illustrates a schematic view of the lower vessel inserted with its division plates therein in the lower vessel as to separate the homogeneous sample in a plurality of samples.

FIG. 2 illustrates the apparatus of the present invention in operation wherein the lower vessel 2 is arranged under the upper vessel 1 and wherein, the upper portion of the division plates 12 are located within the slots 8 at floor level of the upper vessel 1. The material 15 is fed by the feeder 3 which completes an oscillating movement 14 above the open ceiling 7 of the upper vessel 1. The oscillating movement 14 from a first end of the upper vessel 1 to a second end of the upper vessel 3 (FIG. 3) ensures that within the upper vessel a heap of material is formed as per the method of Chevron. Once the material 15 shaped as a Chevron heap is formed within the upper vessel 1, the lower vessel 2 is raised as to make the division plates 12 divide the heap of material 15 in partitions as shown in FIG. 4.

Figure 5:
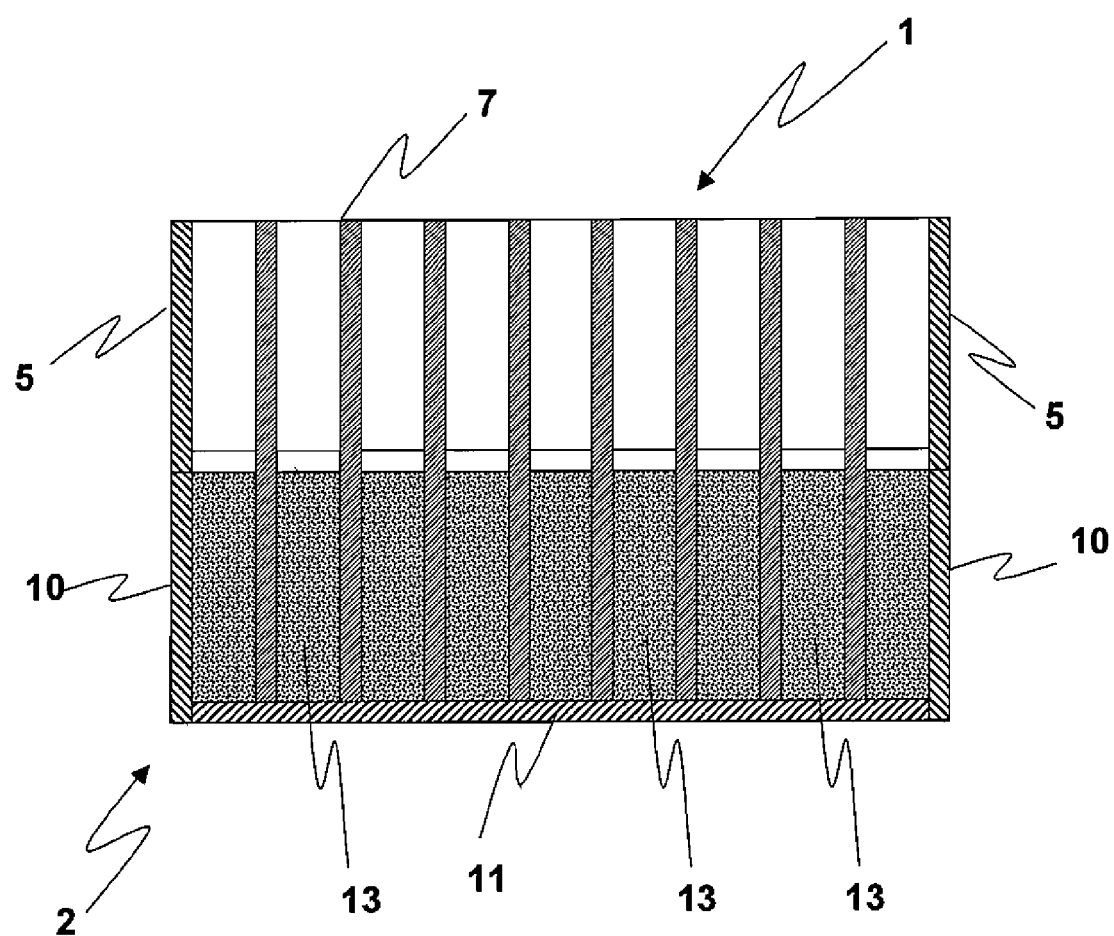
FIG. 5 illustrates a schematic view of the lower vessel inserted with the division plates therein in the lower vessel wherein the homogeneous sample has been separated in a plurality of samples which fall on the lower vessel by removal of the plurality of planks that comprise the floor of the upper vessel.
Figure 6:
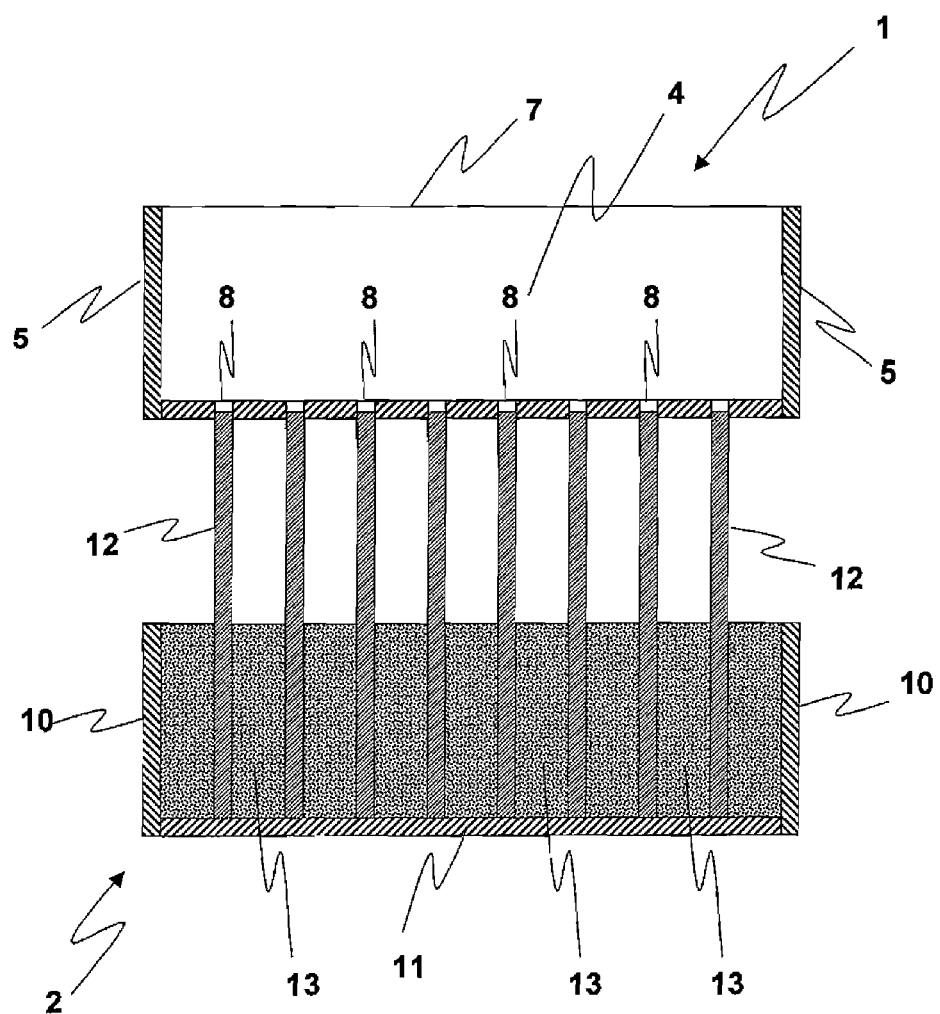
FIG. 6 illustrates a schematic view of the lower vessel isolated from the upper vessel, thus arranging the plurality of samples positioned in the lower vessel ready to be removed for storage and/or analysis.

In order to store the divided heaps, the plurality of planks 6 are removed from the upper vessel 1 thus making the plurality of samples fall toward the compartments 13 of the lower vessel 2 as illustrated in FIG. 5.

Both the upper and lower vessel 1, 2 are separated as to remove the samples and have them ready for further analysis and/or storage.

The samples can be removed through two alternatives: 1) A vessel with the same size of the compartment can be placed within the compartment 13 as to, once the sample drops, remove each vessel; and 2) the floor 11 of the lower vessel can comprise gates (not shown) similar to the planks 6 of the upper vessel which when open allow the samples to fall over any vessel for storage and transport.

The apparatus of the present invention operates as per the following method:

Positions of the lower vessel 2 under the upper vessel 1 wherein, the upper portion of the division plates 12 is positioned within the slots 8 at the level of the floor of the upper vessel 1 in a way that the upper vessel can receive the material 15 fed by the feeder 3;

Feeds the material to sample through the feeder 3 by an oscillating movement 14 wherein the movement and speed of the feeder have been calculated previously;

Forms a heap of Chevron within the upper vessel 1;

Raises the lower vessel in a way that the division plates partition the heap of the material as to form a plurality of the samples;

Removes the plurality of planks 6 from the upper vessel 1, thus making the plurality of samples fall toward the compartments 13 of the lower vessel 2 as to store the partitioned heaps;

Separates both the upper and lower vessel as to remove the samples and have them ready for further analysis and/or storage.

What is claimed is:

1. An apparatus for preparing samples of granulated material comprising:
    an upper vessel which has a floor consisting of a plurality of planks each of them with a slot between therein, and the ceiling of the upper vessel is open as to allow passing of homogenized material;
    a lower vessel arranged under the upper vessel wherein the lower vessel has inside therein a plurality of division plates which are taller in height than the walls of the lower vessel; wherein said division plates fit in the slots of the upper vessel; wherein the division plates form within the lower vessel a plurality of compartments that will hold the plurality of samples; and
    a feeder which has an oscillating movement over the upper surface of the upper vessel and which movement and speed had been previously computed as to ensure rendering of a homogenised and representative sample as per the method of Chevron.

2. The apparatus according to claim 1 wherein the lower vessel is arranged under the upper vessel and the upper portion of the division plates is positioned within the slots leveled with the floor of the upper vessel in a way that the upper vessel can receive the material fed by the feeder.

3. The apparatus according to claim 2 wherein the feeder completes an oscillating movement above the open ceiling of the upper vessel.

4. The apparatus according to claim 1 wherein within each compartment it is possible to arrange a vessel of the same size of the compartment, wherein said vessel is used for removal of the samples from the apparatus.

5. The apparatus according to claim 1 wherein the floor of the lower vessel can consist of gates which, when open allow the samples to fall over any vessel for storage and transport purposes.

6. A method for preparing samples of granulated material comprising the steps of:
    providing an upper vessel which has a floor consisting of a plurality of planks each of them with a slot between therein, and the ceiling of the upper vessel is open as to allow passing of homogenized material;
    providing a lower vessel which is located under the upper vessel wherein the lower vessel has inside therein a plurality of division plates which are taller in height than the walls of the lower vessel; wherein said division plates fit in the slots of the upper vessel; wherein the division plates form within the lower vessel a plurality of compartments that will hold the plurality of samples;
    providing a feeder which has an oscillating movement over the upper surface of the upper vessel and which movement and speed had been previously computed as to ensure rendering of a homogenised and representative sample as per the method of Chevron;
    positioning of the lower vessel under the upper vessel wherein, the upper portion of the division plates is positioned within the slots at the level of the floor of the upper vessel in a way that the upper vessel can receive the material fed by the feeder;
    feeding the material to sample through the feeder by an oscillating movement wherein the movement and speed of the feeder have been calculated previously;
    forming a heap of Chevron within the upper vessel;
    raising the lower vessel in a way that the division plates partition the heap of the material as to form a plurality of the samples;
    removing the plurality of planks from the upper vessel thus making the plurality of samples fall toward the compartments of the lower vessel as to store the partitioned heaps; and
    separating both the upper and lower vessel as to remove the samples and have them ready for further analysis and/or storage.

* * * * *